United States Patent
Bak et al.

(10) Patent No.: US 11,238,982 B2
(45) Date of Patent: Feb. 1, 2022

(54) MANAGING MEDICAL EVENTS USING VISUAL PATTERNS GENERATED FROM MULTIVARIATE MEDICAL RECORDS

(71) Applicant: INTERNATIONAL BUSINESS MACHINES CORPORATION, Armonk, NY (US)

(72) Inventors: Peter Bak, Yokneam Ilit (IL); Avi Yaeli, Ramot Menashe (IL)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 376 days.

(21) Appl. No.: 15/867,766

(22) Filed: Jan. 11, 2018

(65) Prior Publication Data
US 2019/0214131 A1    Jul. 11, 2019

(51) Int. Cl.
*G16H 40/63*    (2018.01)
*G16H 10/60*    (2018.01)
(Continued)

(52) U.S. Cl.
CPC .......... *G16H 40/63* (2018.01); *G16H 10/60* (2018.01); *G06T 11/206* (2013.01); *G06T 2200/24* (2013.01); *G16H 15/00* (2018.01)

(58) Field of Classification Search
CPC ........ G16H 40/63; G16H 10/60; G16H 15/00; G06T 11/206; G06T 2200/24
See application file for complete search history.

(56) References Cited

U.S. PATENT DOCUMENTS 8,862,196 B2 * 10/2014 Lynn .................. A61B 7/003
                                                           600/323
9,233,255 B2    1/2016 Powers
(Continued)

FOREIGN PATENT DOCUMENTS

CA    2864522 C    9/2015
CA    2874768 A    10/2018
(Continued)

OTHER PUBLICATIONS

Gotz, David et al. "A methodology for interactive mining and visual analysis of clinical event patterns using electronic health record data", http://www.sciencedirect.com/science/article/pii/S1532046414000094; ELSEVIER; downloaded Jul. 13, 2017; pp. 1-29.
(Continued)

*Primary Examiner* — Jonathan Durant
*Assistant Examiner* — Anne-Marie K Alderson
(74) *Attorney, Agent, or Firm* — Cantor Colburn LLP; Steven Bouknight

(57) ABSTRACT

A system for managing medical events, includes: at least one medical sensor, configured to output a plurality of sensor measurements; at least one display; at least one hardware processor connected to the medical sensor and the display, and adapted to: receive a plurality of events, each having a time of occurrence, including the plurality of measurements and a plurality of external events; identify a target sequence of events in the plurality of events; identify in the plurality of events a plurality of matching sequences, each including a sequence of events matching the target sequence; augment each of the matching sequences with some temporally related events according to a predefined time test; cluster the plurality of augmented sequences in a plurality of clusters according to a temporal distribution of events; and display
(Continued)

on the display a visual representation of the plurality of clusters according to a predefined set of similarity criteria.

12 Claims, 6 Drawing Sheets

(51) Int. Cl.
*G16H 15/00* (2018.01)
*G06T 11/20* (2006.01)

(56) References Cited

U.S. PATENT DOCUMENTS

| | | | |
|---|---|---|---|
| 9,549,253 B2 | 1/2017 | Alexandridis et al. | |
| 9,848,058 B2* | 12/2017 | Johnson | H04L 45/308 |
| 10,032,526 B2* | 7/2018 | Lynn | G16H 10/60 |
| 2009/0216555 A1* | 8/2009 | Mitchell | G16H 10/60 |
| | | | 705/3 |
| 2010/0022847 A1* | 1/2010 | Crowley | G06F 19/3418 |
| | | | 600/300 |
| 2013/0103719 A1 | 4/2013 | Gotz et al. | |
| 2013/0338453 A1* | 12/2013 | Duke | A61B 5/14532 |
| | | | 600/309 |
| 2014/0350961 A1 | 11/2014 | Csurka et al. | |
| 2015/0106022 A1 | 4/2015 | Gotz et al. | |
| 2015/0294088 A1 | 10/2015 | Walker et al. | |
| 2016/0103960 A1* | 4/2016 | Hume | G16H 40/63 |
| | | | 705/2 |
| 2016/0192848 A1* | 7/2016 | Ravishankar | G16H 50/30 |
| | | | 340/573.1 |
| 2016/0328526 A1* | 11/2016 | Park | G06N 20/00 |

FOREIGN PATENT DOCUMENTS

| | | |
|---|---|---|
| CN | 104244754 A | 12/2014 |
| WO | 2014204966 A | 12/2014 |

OTHER PUBLICATIONS

Huang, Chih-Wei et al. "A richly interactive exploratory data analysis and visualization tool using electronic medical records" Accepted: Nov. 2, 2015; Published: Nov. 12, 2015; BMC Medical Informatics and Decision Making 2015 15:92; https://bmcmedinformdecismak.biomedcentral.com/articles/10.1186/s12911-015-0218-7; pp. 1-21.

Wongsuphasawat, Krist et al., "LifeFlow: Visualizing an Overview of Event Sequences", CHI 2011, May 7-12, 2011, Vancouver, BC, Canada; pp. 1747-1756.

* cited by examiner

MANAGING MEDICAL EVENTS USING VISUAL PATTERNS GENERATED FROM MULTIVARIATE MEDICAL RECORDS

BACKGROUND

The present invention, in some embodiments thereof, relates to a system for managing events and, more specifically, but not exclusively, to a system for managing medical events.

Data visualization is a general term that describes any effort to help people understand the significance of data by placing it in a visual context. Patterns, trends and correlations that might go undetected in text-based data may be exposed and recognized easier with visualization of the data. Data retrieval and visualization tools are becoming important in making data-driven insights available to workers throughout an organization.

Specifically, but not exclusively, this holds true with regards to data comprising medical information. Some medical professionals, for example medical practitioners such as physicians, and non-practitioners such as clinical researchers and medical policy makers, need a means for retrieving and viewing information regarding patient treatment management in order to identify one or more aspects of the patient treatment. For example, a physician may have a need to identify an aspect of the patient treatment requiring modification. Another example is a medical policy maker who may require identifying a preferred protocol for treatment from a plurality of possible protocols. A system for managing medical records recording a plurality of medical events, such as electronic medical record (EMR) management systems, may contain vast amounts of data that is of great interest to the medical professionals. There is an increasing need to find visualization methods to extract meaningful information from the vast amounts of data. Appropriate visualization of the plurality of medical events may help compare differences between a certain patient's treatments in one or more time periods or differences between patient groups determine one or more critical factors in treatment of a certain disease or uncover other information hidden in the vast amounts of data.

SUMMARY

It is an object of the present invention to provide a system and a method for managing events and, more specifically, but not exclusively, to a system for managing medical events by visually classifying temporal patterns in multi-variate event sequences.

The foregoing and other objects are achieved by the features of the independent claims. Further implementation forms are apparent from the dependent claims, the description and the figures.

According to a first aspect of the present invention, a system for managing medical events comprises: at least one medical sensor, configured to monitor one or more patients and output a plurality of sensor measurements; at least one display; at least one hardware processor connected to the at least one medical sensor and the at least one display, and adapted to: receive a plurality of events, each having a time of occurrence, comprising the plurality of sensor measurements and a plurality of external events pertaining to the one or more patients and received from an external database; identify a target sequence of target events in the plurality of events; identify in the plurality of events a plurality of matching sequences, each comprising a sequence of events matching the target sequence according to at least one identified matching criterion; augment each of the plurality of matching sequences with some temporally related events of the plurality of events according to a predefined time test; cluster the plurality of augmented matching sequences in a plurality of event clusters according to a temporal distribution of events of each augmented matching sequence in a plurality of time intervals according to an event's time of occurrence relative to a time of occurrence of the matching sequence; and display on the at least one display a visual representation of the plurality of event clusters according to a predefined set of similarity criteria.

According to a second aspect of the present invention, a method for managing medical events comprises: receiving a plurality of events, each having a time of occurrence, comprising a plurality of sensor measurements received from at least one medical sensor and a plurality of external events pertaining to one or more patients and received from an external database; identifying a target sequence of target events in the plurality of events; identifying in the plurality of events a plurality of matching sequences, each comprising a sequence of events matching the target sequence according to at least one identified matching criterion; augmenting each of the plurality of matching sequences with some temporally related events of the plurality of events according to a predefined time test; clustering the plurality of augmented matching sequences in a plurality of event clusters according to a temporal distribution of events of each augmented matching sequence in a plurality of time intervals according to an event's time of occurrence relative to a time of occurrence of the matching sequence; and displaying on at least one display a visual representation of the plurality of event clusters according to a predefined set of similarity criteria.

With reference to the first and second aspects, in a first possible implementation of the present invention the at least one hardware processor is adapted to cluster the plurality of augmented matching sequences by: assigning the sequence time of occurrence to each augmented matching sequence of the plurality of augmented matching sequences according to a time of occurrence of at least one event in the augmented matching sequence; computing for each event in each augmented matching sequence of the plurality of augmented matching sequences a relative time of occurrence, relative to the sequence time of occurrence of the augmented matching sequence; sorting, in each of the plurality of augmented matching sequences, the matching sequence's plurality of events into the plurality of time intervals according to the relative time of occurrence; and clustering the plurality of augmented matching sequences into a plurality of event clusters according to a predefined similarity test applied to a distribution of the augmented matching sequence's events in the plurality of time intervals. Augmenting target sequences of events with other events according to a relative time of occurrence may facilitate access to an event's context without requiring separate query and retrieval.

With reference to the first and second aspects, or the first possible implementation of the present invention, in a second possible implementation of the present invention at least one time interval of the plurality of time intervals is shorter than at least one other time interval of the plurality of time intervals. A first plurality of absolute values of a first plurality of times in the at least one other time interval are greater than a second plurality of absolute values of a second plurality of times in the at least one time interval. When a time interval close in time relative to a target event is shorter than a time interval farther in time relative to the target event, events occurring in the time interval close to the target event may be given greater saliency than events occurring in the farther time interval.

With reference to the first and second aspects, in a third possible implementation of the present invention each of the plurality of events has a plurality of values of a plurality of attributes selected from a group of attributes consisting of: a patient identifier, a day of week, a time of day, a medical occurrence, a measured blood sugar value, a measured blood pressure value, a medication identifier, and a medication dosage.

With reference to the first and second aspects, or the third possible implementation of the present invention, in a fourth possible implementation of the present invention the medical occurrence is one of: a blood sugar value exceeding a threshold high blood sugar value, a blood sugar value less than a threshold low blood sugar value, a blood pressure value exceeding a threshold high blood pressure value, a blood pressure value less than a threshold low blood pressure value, a blood sugar value greater than a previous blood sugar value, a blood sugar value less than a previous blood sugar value, a blood pressure value greater than a previous blood pressure value, and a blood pressure value less than a previous blood pressure value. Optionally, the at least one identified matching criterion comprises one or more of a group consisting of: a patient identifier of an event of the sequence of events is equal to another patient identifier of a target event of the target sequence, a day of week of an event of the sequence of events is equal to another day of week of a target event of the target sequence, a time of day of an event of the sequence of events is equal to another time of day of a target event of the target sequence, and a medical occurrence of an event of the sequence of events is equal to another medical occurrence of a target event of the target sequence. Considering one of a plurality of matching criteria when clustering may provide a practitioner with more information than possible when clustering according to only one fixed criterion, without requiring additional event retrieval.

With reference to the first and second aspects, in a fifth possible implementation of the present invention the at least one hardware processor is further adapted to produce a report of the plurality of event clusters. Producing a report is useful for referring to previously computed results without requiring repeated computation.

With reference to the first and second aspects, in a sixth possible implementation of the present invention the at least one hardware processor is further adapted to: execute an electronic medical record (EMR) management system for storing a plurality of events comprising one or more sensor measurements; store the plurality of sensor measurements in the EMR management system; and retrieve the plurality of sensor measurements from the EMR management system. Using an EMR management system allows applying the present invention to existing medical systems to enhance their usability.

With reference to the first and second aspects, in a seventh possible implementation of the present invention the visual representation comprises: for each of one or more of the plurality of event clusters displaying in a common display area of the at least one display a cluster visual representation of some of the event cluster's plurality of events. Optionally, the visual representation further comprises: receiving an instruction from a user to expand one of the plurality of event clusters; and displaying some more of the plurality of events of at least one of the plurality of event clusters. Enabling a user to expand a cluster to display some more events allows a practitioner speedier access to a context of one or more events than possible when a separate access to the plurality of events is required. Optionally, for each cluster of the plurality of event clusters the cluster visual representation comprises displaying a first graphic object for a first plurality of events of a first of the plurality of augmented matching sequences of the cluster, and a second graphic object for a second plurality of events of a second of the plurality of augmented matching sequences of the cluster. Optionally, the cluster visual representation is displayed on a graph having one axis representing a time according to the relative time of occurrence of each of the plurality of events.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
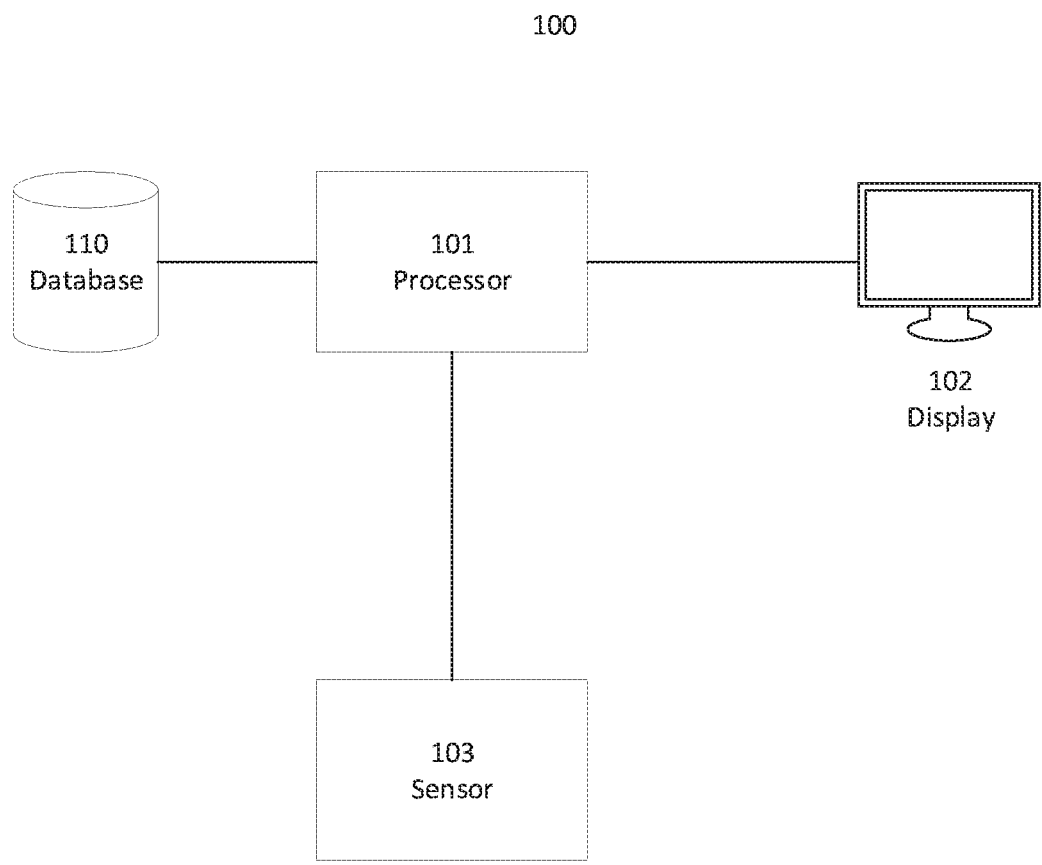
FIG. 1 is a schematic block diagram of an exemplary system, according to some embodiments of the present invention.

The present invention, in some embodiments thereof, relates to a system for managing events and, more specifically, but not exclusively, to a system for managing medical events.

The following description focuses on the use of the present invention in a system for managing medical events, but the present invention is not limited to such systems, and may be used to manage events of another field, for example usage and service logs of mechanical components, manufacturing processes, and agricultural processes.

It may be the case that it is of interest to identify one or more patterns in a plurality of events, i.e. a plurality of similar sequences of events. There exist data analysis tools that identify one or more patterns according to an event type of the plurality of events. For example, when the plurality of events comprise a plurality of medical events, a first sequence of events may be considered similar to a second sequence of events when the first sequence of events comprises a certain sequence of medical event types and the second sequence of events comprises the same certain sequence of medical event types or the same certain sequence of similar medical event types, according to an event type similarity test. For example, a case where in a plurality of similar sequences of events, in each of the similar sequences an event of administration of a medication is followed by an event of a decrease in a blood pressure value followed by an event of an increase in a blood pressure value.

Some existing data analysis tools, that may be used to graphically show medical associations over time, produce a set of summary elements and graphically visualize the set of summary elements. Such tools may analyze the plurality of medical events to identify one or more identified patterns of events. The set of summary elements may comprise the one or more identified patterns of events, with each summary element representing one or more of the plurality of medical events in an identified pattern. Such visualization is useful for displaying one or more patterns and trends in the plurality of events, however in such data analysis tools information of an individual event used to produce the set of summary elements is lost and a user is unable to view data of an individual event, in the individual event's context. Thus, when the individual event is one of a continuous stream of events, obtained for example by continuous measurements of a medical parameter such as a blood pressure value or a blood sugar value, received from a medical sensor monitoring one or more patients, additional information that may be garnered from the individual event's context in the stream of events is lost in a visualization of a set of summary elements as the event's context is not preserved in the set of summary elements. Retrieving the event's context requires separate access to the plurality of events to search and retrieve other events in the context of the event.

In addition, patterns based on a similarity in the sequence of event types are useful but insufficient. It may be the case that temporal distribution of the plurality of events in a sequence of events is of significance. For example, it may be of interest to identify when an increase in a blood pressure value occurs immediately after a decrease in blood pressure value following administration of a first medication, but not following administration of a second medication. In this example, when these patterns are identified in the one patient a physician may identify that the second medication is more suitable for one patient, Alternately, when these patterns are identified in more than one patient the physician may identify that the second medication is more suitable for a plurality of patients. Existing data analysis tools do not offer identifying temporal similarity.

As used henceforth, the term "multi-variate event" means an event having a plurality of values of a plurality of attributes. We hereby disclose a system and a method for managing a plurality of events comprising a plurality of multi-variate event sequences, including but not limited to a plurality of medical events, using visual classification of temporal patterns that preserves an individual event's context within the plurality of medical events. In some embodiments of the present invention, the individual context's event is preserved by organizing the plurality of events in a plurality of event clusters and displaying the plurality of event clusters. Initially the system may display for one or more event clusters a summary of the event cluster or some of the event cluster's events; however the user may instruct expansion of an event cluster to display one or more additional events of the event cluster, where the one or more additional events are part of a context of one of the event clusters' events. In some embodiments of the present invention, the plurality of events is organized in the plurality of event clusters according to a similarity of a temporal distribution of some events in a plurality of event sequences. Organizing the plurality of events according to a similarity in temporal distribution may provide useful information not available from similarity in event type sequence alone. Existing data analysis tools do not offer identifying temporal similarity, thus the present invention in some embodiments thereof, by identifying temporal similarity and providing a user information about the temporal similarity, improves the user's speed in drawing conclusions and improves accuracy of the drawn conclusions by enabling the user to incorporate information regarding temporal similarity in the user's considerations. In addition, the present invention in some embodiments thereof offers increased usability over other solutions by enabling a user to see an individual event in context of other events, providing a single presentation of an event and its context and eliminating the need to retrieve and display the other events separately.

In addition, in some embodiments of the present invention one or more patterns in the plurality of events are identified according to similarity criteria additional to event type sequence and temporal distribution of events in an event sequence. Each event may have a plurality of values of a plurality of attributes and similarity criteria may be according to any one or more of the plurality of attributes. For example, similarity may be identified according to an event's day of week or time of day. A richer set of event attributes enables identifying complex patterns, invisible when analyzing type of event alone. Existing data analysis tools do not exploit characteristics of multi-variate events and do not offer identifying similarity according to criteria beyond event type, thus the present invention in some embodiments thereof offers improved usability compared to existing data analysis tools by providing the user with a presentation of patterns according to a rich set of similarity criteria not available in existing data analysis tools.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1, showing a schematic block diagram of an exemplary system 100, according to some embodiments of the present invention. In such embodiments, at least one hardware processor 101 is connected to one or more sensors 103 configured to output a plurality of sensor measurements. In embodiments used for managing medical events, one or more sensors 103 are medical sensors, configured to monitor one or more patients. Optionally the one or more patients are monitored as part of treatment of a medical condition or disease. Examples of medical conditions are diabetes, a heart disease and a chronic kidney disease. Optionally the one or more sensors are configured to monitor a plurality of patients, for example, a blood pressure sensor used to measure blood pressure of a plurality of patients. Optionally, the one or more sensors are configured to monitor a single patient, for example a personal blood sugar sensor used by one patient. Optionally, the one or more sensors are configured to continuously monitor one or more patients, for example a Holter monitor. Optionally, the one or more sensors are a wearable device. Optionally, at least one hardware processor 101 is adapted to receive a plurality of events from one or more sensors 103 regarding the one or more patients, comprising the plurality of sensor measurements output by the one or more sensors. For example, where one or more sensors are configured to monitor a patient being treated for diabetes, some of the events may comprise information about a measured blood sugar value. In addition, at least one hardware 101 may receive external events pertaining to the one or more patients. Examples of external events are demographic information such as a patient's gender and a patient's age, and behavioral information such as food consumed by the one or more patients, and activities performed by the one or more patients, for example sleep and exercise. Optionally, at least one hardware processor is connected to a database 110 and the plurality of external events is received from database 110. Each of the events may have a plurality of values of a plurality of attributes. Examples of attributes are a patient identifier, an age, a gender, a time of occurrence, a day of week, a time of day, a medical occurrence identifier, a measured blood sugar value, a measured blood pressure value, a medication identifier, and a medication dosage.

Optionally, at least one hardware processor 101 is connected to one or more displays 102, for the purpose of displaying a visual representation of the plurality of events on one or more displays 102. A medical practitioner may use the visual representation to identify a need to modify a medical treatment procedure. A medical administrator may use the visual representation to learn information to be used in decisions regarding medical policy.

In some embodiments of the present invention, at least one hardware processor 101 executes an Electronic Record Management (ERM) system. Optionally, the at least one hardware processor stores the plurality of medical events in the ERM system and retrieves the plurality of medical events from the ERM system in order to produce and display the visual representation of the plurality of medical events.

To produce and display a visual representation of the plurality of events, comprising the plurality of medical events and the plurality of external events, in some embodiments of the present invention at least one hardware processor 101 implements the following optional method.

Figure 2:
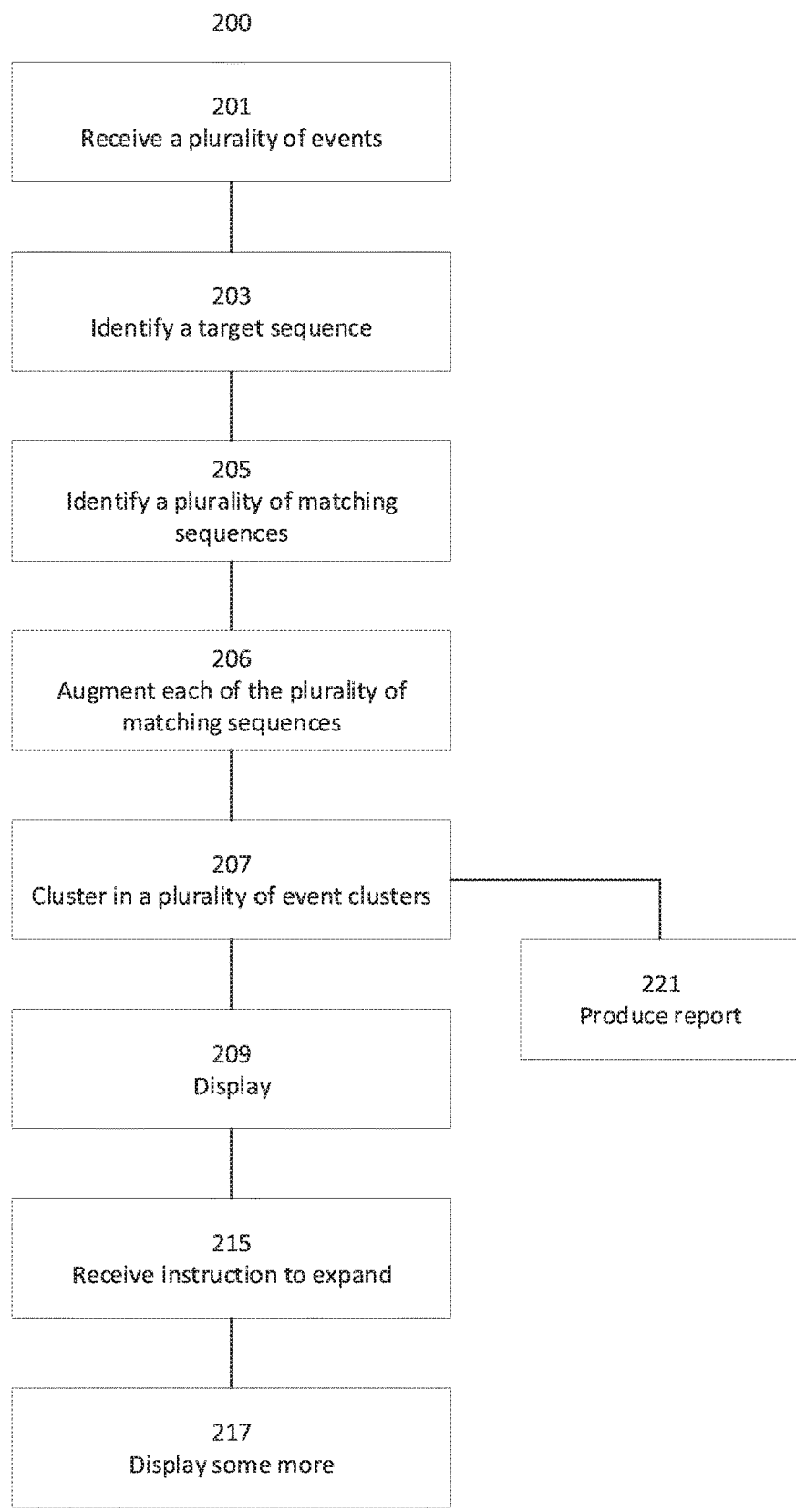
FIG. 2 is a flowchart schematically representing an optional flow of operations for managing medical events, according to some embodiments of the present invention.

Reference is now made also to FIG. 2 showing a flowchart schematically representing an optional flow of operations 200 for managing medical events, according to some embodiments of the present invention. In such embodiments, at least one hardware processor 101 receives in 201 a plurality of events. Optionally, the plurality of events comprises a plurality of sensor measurements, received from one or more medical sensors 103. Optionally, the plurality of events comprises a plurality of external events. Optionally, each of the plurality of events has a plurality of values of a plurality of attributes. Examples of attributes are: a patient identifier, an age, a gender, a time of occurrence, a day of week, a time of day, a medical occurrence identifier, a measured blood sugar value, a measured blood pressure value, a medication identifier, and a medication dosage. Examples of a medical occurrence are: a blood sugar value exceeding a threshold high blood sugar value, a blood sugar value less than a threshold low blood sugar value, a blood pressure value exceeding a threshold high blood pressure value, a blood pressure value less than a threshold low blood pressure value, a blood sugar value greater than a previous blood sugar value, a blood sugar value less than a previous blood sugar value, a blood pressure value greater than a previous blood pressure value, and a blood pressure value less than a previous blood pressure value.

Next, in 203 the one or more hardware processor identifies in the plurality of events a target sequence of target events. For example, a target sequence comprises one target event of administration of a medication followed by a second target event of a measured blood sugar value. A target sequence may be identified manually. Optionally, at least one hardware processor applies a frequent pattern analysis method as known in the art to the plurality of events to identify the target sequence. In 205, the at least one hardware processor optionally identifies in the plurality of events a plurality of matching sequences, where each matching sequence optionally comprises a sequence of events matching the target sequence according to a least one identified matching criterion. The at least one identified matching criterion optionally comprises identifying that an event's medical occurrence identifier equals a certain medical occurrence identifier, for example a measured blood sugar value. The at least one identified matching criterion optionally comprises a result of a comparison of a value of an identified attribute of an event to a certain threshold value, for example a measured blood sugar value exceeds a certain threshold measured blood sugar value. Other examples of a matching criterion are: a patient identifier of an event of the sequence of events is equal to another patient identifier of a target event of the target sequence, a day of week of an event of the sequence of events is equal to another day of week of a target event of the target sequence, a time of day of an event of the sequence of events is equal to another time of day of a target event of the target sequence, and a medical occurrence of an event of the sequence of events is equal to another medical occurrence of a target event of the target sequence.

In 206, at least one hardware processor 101 optionally augments each of the plurality of matching sequences with some temporally related events of the plurality of events, according to a predefined time test. The temporally related events are part of the matching sequence's context in the plurality of events, and augmenting a matching sequence with its context facilitates displaying richer information about the matching sequence than when displaying events of the matching sequence alone.

Optionally, in 207 the at least one hardware processor clusters the plurality of augmented matching sequences in a plurality of event clusters, according to a temporal distribution of events if each augmented matching sequence in a plurality of time intervals according to an event's time of occurrence relative to a time of occurrence of the matching sequence. Using the relative time of occurrence to organize the plurality of augmented matching sequences into a plurality of event clusters facilitates identifying temporal similarity between some sequences of events of the plurality of events and at least one of the identified targets. To organize the plurality of events into such event clusters, at least one hardware processor 101 optionally implements the following optional method.

Figure 3:
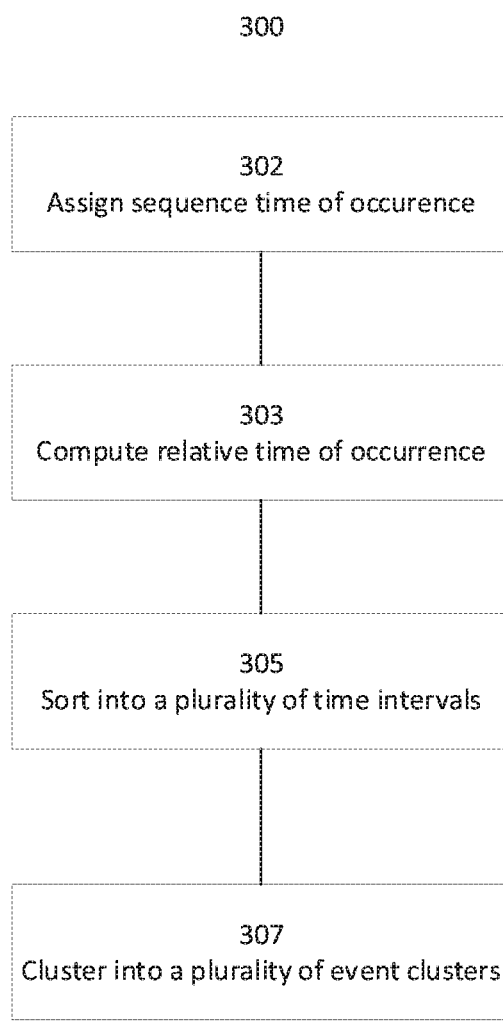
FIG. 3 is a flowchart schematically representing an optional flow of operations for clustering, according to some embodiments of the present invention.

Reference is now made also to FIG. 3, showing a flowchart schematically representing an optional flow of operations 300 for clustering a plurality of augmented matching sequences, according to some embodiments of the present invention. In such embodiments, in 302 the at least one hardware processor assigns the sequence time of occurrence to each augmented matching sequence of the plurality of augmented matching sequences according to a time of occurrence of at least one event in the augmented matching sequence. Next in 303 the at least one hardware processor optionally computes for each event in each augmented matching sequence a relative time of occurrence, relative to the augmented matching sequence's sequence time of occurrence. Using relative times facilitates identifying temporal patterns in the plurality of events. In 305 the at least one hardware processor optionally sorts, in each of the plurality of augmented matching sequences, the matching sequence's plurality of events into the plurality of time intervals according to the relative time of occurrence of each of the plurality of events. This process is known in the art as binning. Binning allows grouping together events occurring within one or more predefined time intervals. Using a plurality of time intervals having a plurality of different lengths may facilitate giving some events greater saliency than other events. An event sorted into one time interval having a first length may have a greater saliency than an event sorted into a second interval having a second length greater than the first length. An absolute value of an event's relative time of occurrence may indicate how temporally close the event is to the target sequence regardless of whether the event occurred before, during, or after the target sequence. There may be a need to give events saliency occurring in temporal proximity to the identified target. A first time interval having a first range of absolute values of relative times greater than a second range of absolute values of relative times of a second time interval may be considered temporally closer to the identified target. Optionally, at least one time interval closer to the identified target than another time interval has a shorter length than the other time interval, that is events sorted in to the at least one time interval may have greater saliency. In 307, the at least one hardware processor optionally clusters the plurality of augmented matching sequences into a plurality of event clusters according to a predefined similarity test applied to a distribution of an augmented matching sequence's events in the plurality of time intervals. As a result, each of the resulting plurality of event clusters may comprise a plurality of augmented matching sequences similar not only in a sequence of event types but in a temporal pattern as well. Optionally, the at least one hardware processor optionally clusters the plurality of augmented matching sequences into a plurality of other event clusters according to an identified test, other than temporal similarity, applied to the plurality of events' plurality of values of the plurality of attributes. For example, according to comparing the plurality of events' plurality of values of an identified attribute to a plurality of identified threshold attribute values.

Reference is now made again to FIG. 2. In 209, the at least one hardware processor optionally displays a visual representation of the plurality of event clusters. Optionally the at least one hardware processor displays the visual representation on one or more displays 102. Optionally, the visual representation is according to a predefined set of similarity criteria. Optionally, for each of one or more of the plurality of event clusters, at the least one hardware processor displays a cluster visual representation of at least some of the event cluster's plurality of events.

Figure 4A:
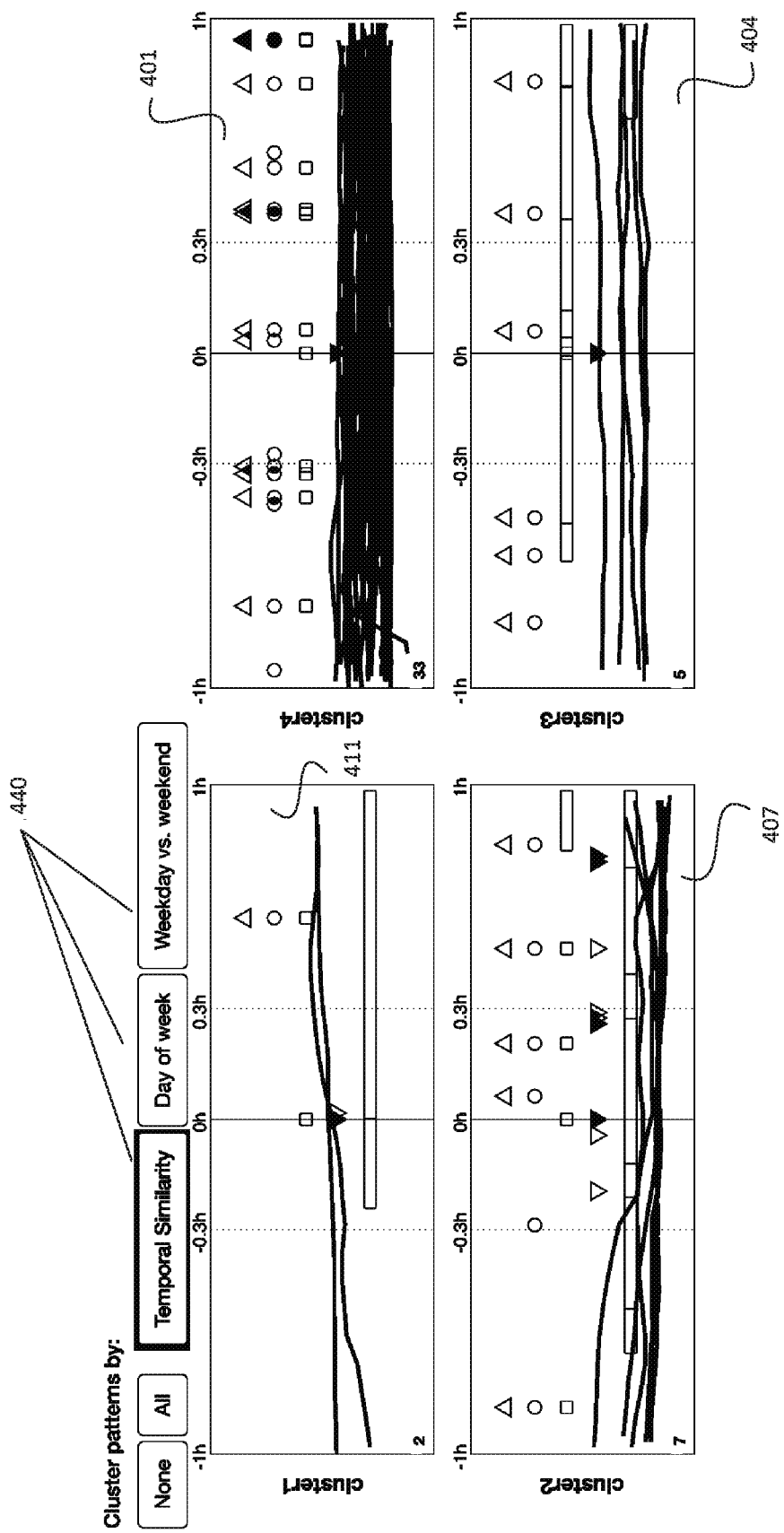
FIGS. 4A, 4B and 4C are exemplary screen shots of a visual representation, according to some embodiments of the present invention.
Figure 4B:
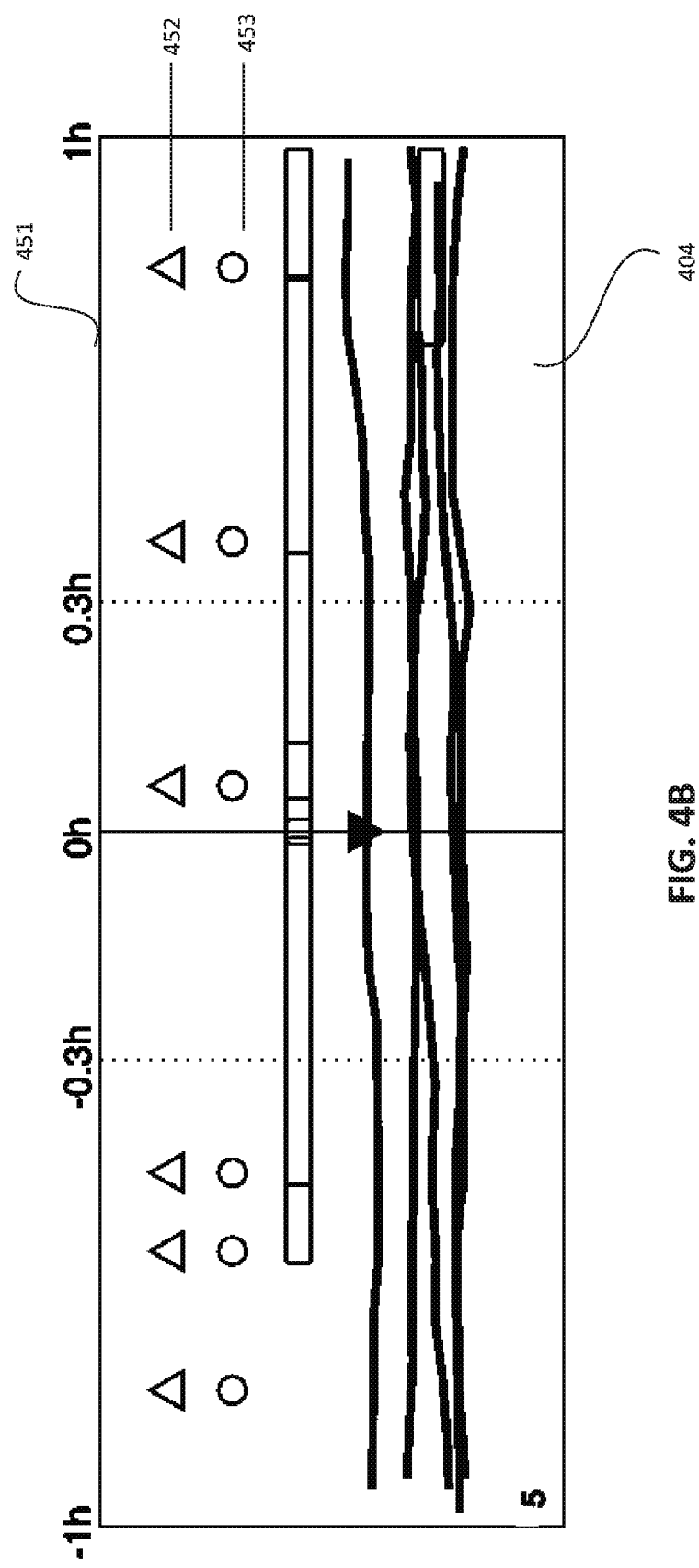
Figure 4C:
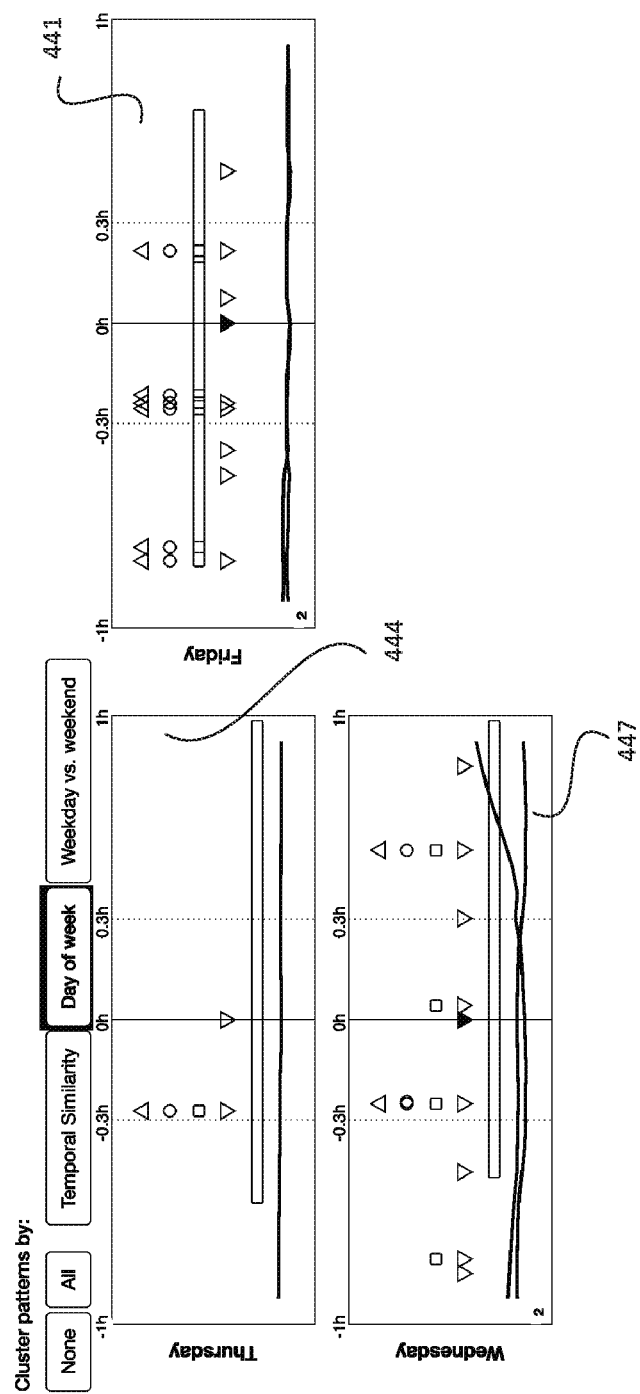

Reference is now made also to FIGS. 4A, 4B and 4C, showing exemplary screen shots of a visual representation, according to some embodiments of the present invention. FIG. 4A shows exemplary common display areas 401, 404, 407 and 411. Each display area comprises a cluster visual representation of one of the plurality of event clusters. Optional buttons 440 may be used by a user to select a display similarity criterion other than temporal similarity, for example display according to day of week, or display according to weekdays vs. weekends. Reference is now also made to FIG. 4B, showing exemplary common display area 404 in detail. Optionally, exemplary common display area 404 displays a cluster visual representation of one event cluster, comprising a plurality of similar augmented matching sequences. Each augmented matching sequence of the event cluster optionally comprises a matching sequence comprising a sequence of events matching a common target sequence, i.e. all event groups of the event cluster are similar to the common target sequence. Optionally, the cluster visual representation has a graph having one axis 451 representing a time according to the relative time of occurrence of each of the plurality of events in the event cluster. Optionally, the cluster visual representation comprises displaying a first graphic object for a first plurality of events of a first augmented matching sequence of the plurality of augmented matching sequences of the event cluster, and a second graphic object for a second plurality of events of a second augmented matching sequence of the plurality of augmented matching sequences of the event cluster. Thus an augmented matching sequence may be visually recognized by graphical object, for example one or more graphical objects 452 and 453. An example of a graphical object is a continuous line, for example to denote a continuous measurement. Another example of a graphical object is a longitudinal bar, for example to denote an event having duration. A graphical object may be a graphical symbol such as a geometrical shape, used for example to denote an event without duration. Optionally, a graphical object is used to represent a plurality of events in one time interval.

Reference is now made again to FIG. 2. In 221 the at least one hardware processor optionally produces a report of the plurality of event clusters.

In 215, the at least one hardware processor may receive an instruction from a user to expand one of the plurality of event clusters. For example, a user might double-click a graphical object using a pointing device. Optionally, in 216 the at least one hardware processor displays some more of the plurality of events of the at least one of the plurality of event clusters. For example, the at least one hardware processor may expand the event cluster display by displaying all events in an augmented matching sequence of a selected event. Optionally, the at least one hardware processor may expand the event cluster display by changing a display scale of a time axis. Optionally, the at least one hardware processor may expand the event cluster display by displaying text describing one or more event's attribute values.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant medical events will be developed and the scope of the term medical event is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for managing medical events, comprising:
at least one medical sensor, configured to monitor one or more patients and output a continuous data stream comprising a plurality of sensor measurements;
at least one display;
at least one hardware processor connected to said at least one medical sensor and said at least one display, and adapted to:
receive a plurality of events, each having a time of occurrence, comprising said plurality of sensor measurements and a plurality of external events pertaining to said one or more patients and received from an external database;
identify a target sequence of target events in said plurality of events, wherein the target sequence comprises a first target event followed by a second target event, the first target event comprising an administration of a medication and the second target event comprising a medical occurrence;
identify in said plurality of events a plurality of matching sequences, each comprising the first target event followed by the second target event;
augment each of said plurality of matching sequences with some temporally related events of said plurality of events;
cluster said plurality of augmented matching sequences in a plurality of event clusters, wherein a portion of the plurality of augmented matching sequences are clustered according to a temporal distribution of events of each augmented matching sequence in a plurality of time intervals according to an event's time of occurrence relative to a time of occurrence of said matching sequence, wherein the plurality of time intervals comprise different durations, wherein a duration of a first time interval closer to a target event of the target sequence is smaller than a duration of a second time interval further from the target event;
display on said at least one display a visual representation of said plurality of event clusters according to a predefined set of similarity criteria, wherein the predefined set of similarity criteria comprises the temporal distribution of events and at least one additional similarity criterion, wherein the display is populated with two or more cluster selection tools, and wherein selecting a first cluster selection tool displays a first cluster pattern comprising the temporal distribution of events, and selecting a second cluster selection tool displays a second cluster pattern comprising an additional similarity criterion of the at least one additional similarity criterion; and
wherein a first medication is associated with a matching sequence and a second medication is not associated with any matching sequences.

2. The system of claim 1, wherein said at least one hardware processor is adapted to cluster said plurality of augmented matching sequences by:
assigning said sequence time of occurrence to each augmented matching sequence of said plurality of augmented matching sequences according to a time of occurrence of at least one event in said plurality of augmented matching sequences;
computing for each event in each augmented matching sequence of said plurality of augmented matching sequences a relative time of occurrence, relative to said sequence time of occurrence of plurality of augmented matching sequences;
sorting, in each of said plurality of augmented matching sequences, said matching sequence's plurality of events into said plurality of time intervals according to said relative time of occurrence; and
clustering the plurality of augmented matching sequences into a plurality of event clusters according to a predefined similarity test applied to a distribution of said plurality of augmented matching sequence's events in said plurality of time intervals.

3. The system of claim 1, wherein each of said plurality of events has a plurality of values of a plurality of attributes selected from a group of attributes consisting of: a patient identifier, a day of week, a time of day, said medical occurrence, a measured blood sugar value, a measured blood pressure value, a medication identifier, and a medication dosage.

4. The system of claim 1, wherein said medical occurrence is one of: a blood sugar value exceeding a threshold high blood sugar value, a blood sugar value less than a threshold low blood sugar value, a blood pressure value exceeding a threshold high blood pressure value, a blood pressure value less than a threshold low blood pressure value, a blood sugar value greater than a previous blood sugar value, a blood sugar value less than a previous blood sugar value, a blood pressure value greater than a previous blood pressure value, and a blood pressure value less than a previous blood pressure value.

5. The system of claim 3, wherein said at least one identified matching criterion comprises one or more of a group consisting of: a patient identifier of an event of said sequence of events is equal to another patient identifier of a target event of said target sequence, a day of week of an event of said sequence of events is equal to another day of week of a target event of said target sequence, a time of day of an event of said sequence of events is equal to another time of day of a target event of said target sequence, and a medical occurrence of an event of said sequence of events is equal to another medical occurrence of a target event of said target sequence.

6. The system of claim 2, wherein at least one time interval of said plurality of time intervals is shorter than at least one other time interval of said plurality of time intervals; and
wherein a first plurality of absolute values of a first plurality of times in said at least one other time interval are greater than a second plurality of absolute values of a second plurality of times in said at least one time interval.

7. The system of claim 1, wherein said at least one hardware processor is further adapted to produce a report of said plurality of event clusters.

8. The system of claim 1, wherein said at least one hardware processor is further adapted to:
execute an electronic medical record (EMR) management system for storing a plurality of events comprising one or more sensor measurements;
store said plurality of sensor measurements in said EMR management system; and retrieve said plurality of sensor measurements from said EMR management system.

9. A method for managing medical events, comprising:

receiving a plurality of events, each having a time of occurrence, comprising a plurality of sensor measurements received from at least one medical sensor and a plurality of external events pertaining to one or more patients and received from an external database;

identifying a target sequence of target events in said plurality of events, wherein the target sequence comprises a first target event followed by a second target event, the first target event comprising an administration of a medication and the second target event comprising a medical occurrence;

identifying in said plurality of events a plurality of matching sequences, each comprising the first target event followed by the second target event, wherein a first medication is associated with a matching sequence and a second medication is not associated with any matching sequences;

augmenting each of said plurality of matching sequences with some temporally related events of said plurality of events;

clustering said plurality of augmented matching sequences in a plurality of event clusters, wherein a portion of the plurality of augmented matching sequences are clustered according to a temporal distribution of events of each augmented matching sequence in a plurality of time intervals according to an event's time of occurrence relative to a time of occurrence of said matching sequence, wherein the plurality of time intervals comprise different durations, wherein a duration of a first time interval closer to a target event of the target sequence is smaller than a duration of a second time interval further from the target event;

displaying on at least one display a visual representation of said plurality of event clusters according to a predefined set of similarity criteria, wherein the predefined set of similarity criteria comprises the temporal distribution of events and at least one additional similarity criterion, wherein the display is populated with two or more cluster selection tools, and wherein selecting a first cluster selection tool displays a first cluster pattern comprising the temporal distribution of events, and selecting a second cluster selection tool displays a second cluster pattern comprising an additional similarity criterion of the at least one additional similarity criterion; and identifying the second medication for a patient over the first medication in response to the first medication being associated with a matching sequence and the second medication not being associated with any matching sequences.

10. The method of claim 9, wherein said visual representation comprises: for each of one or more of said plurality of event clusters displaying in a common display area of said at least one display a cluster visual representation of some of said event cluster's plurality of events.

11. The method of claim 10, further comprising:

receiving an instruction from a user to expand one of said plurality of event clusters; and displaying some more of said plurality of events of at least one of said plurality of event clusters.

12. The method of claim 10, wherein for each cluster of said plurality of event clusters said cluster visual representation comprises displaying a first graphic object for a first plurality of events of a first of said plurality of augmented matching sequences of said cluster, and a second graphic object for a second plurality of events of a second of said plurality of augmented matching sequences of said cluster; and wherein said cluster visual representation is displayed on a graph having one axis representing a time according to said relative time of occurrence of each of said plurality of events.

* * * * *